United States Patent
Gustavsson et al.

(10) Patent No.: US 6,207,188 B1
(45) Date of Patent: Mar. 27, 2001

(54) OMEPRAZOLE SODIUM SALT

(75) Inventors: Anders Gustavsson; Kristina Kjellbom; Ingvar Ymén, all of Södertälje (SE)

(73) Assignee: AstraZeneca AB, Sodertalje (SE)

(*) Notice: Subject to any disclaimer, the term of this patent is extended or adjusted under 35 U.S.C. 154(b) by 0 days.

(21) Appl. No.: 09/101,081
(22) PCT Filed: Jun. 11, 1998
(86) PCT No.: PCT/SE98/01124
§ 371 Date: Jun. 29, 1998
§ 102(e) Date: Jun. 29, 1998
(87) PCT Pub. No.: WO99/00380
PCT Pub. Date: Jan. 7, 1999

(30) Foreign Application Priority Data

Jun. 27, 1997 (SE) .................................. 9702483

(51) Int. Cl.[7] .................. A61K 9/20; A61K 9/48; A61K 9/22; A61K 9/26
(52) U.S. Cl. .................. 424/464; 424/451; 424/452; 424/465; 424/468; 424/469
(58) Field of Search .................. 424/464, 465, 424/451, 452, 468, 469

(56) References Cited

U.S. PATENT DOCUMENTS 4,182,889 * 1/1980 Asai et al. .................. 546/197
5,948,789 * 9/1999 Larsson et al. .................. 514/299

FOREIGN PATENT DOCUMENTS

| 0005129 | 10/1979 | (EP) . |
| 0124495 | 11/1984 | (EP) . |
| 0247983 | 4/1986 | (EP) . |
| 9601623 | 1/1996 | (WO) . |
| 9900380 | 1/1999 | (WO) . |

* cited by examiner

Primary Examiner—Thurman K. Page
Assistant Examiner—S. Tran
(74) Attorney, Agent, or Firm—White & Case LLP

(57) ABSTRACT

This invention relates to a novel form of the sodium salt of 5-methoxy-2-[[(4-methoxy-3,5-dimethyl-2-pyridinyl)methyl]sulfinyl]-1H-benzimidazole, known under the generic name omeprazole sodium salt. This invention also relates to processes for its preparation of omeprazole sodium form B which is thermodynamically stable, as well as pharmaceutical compositions containing it and its use in the treatment of gastrointestinal disorders.

9 Claims, 3 Drawing Sheets

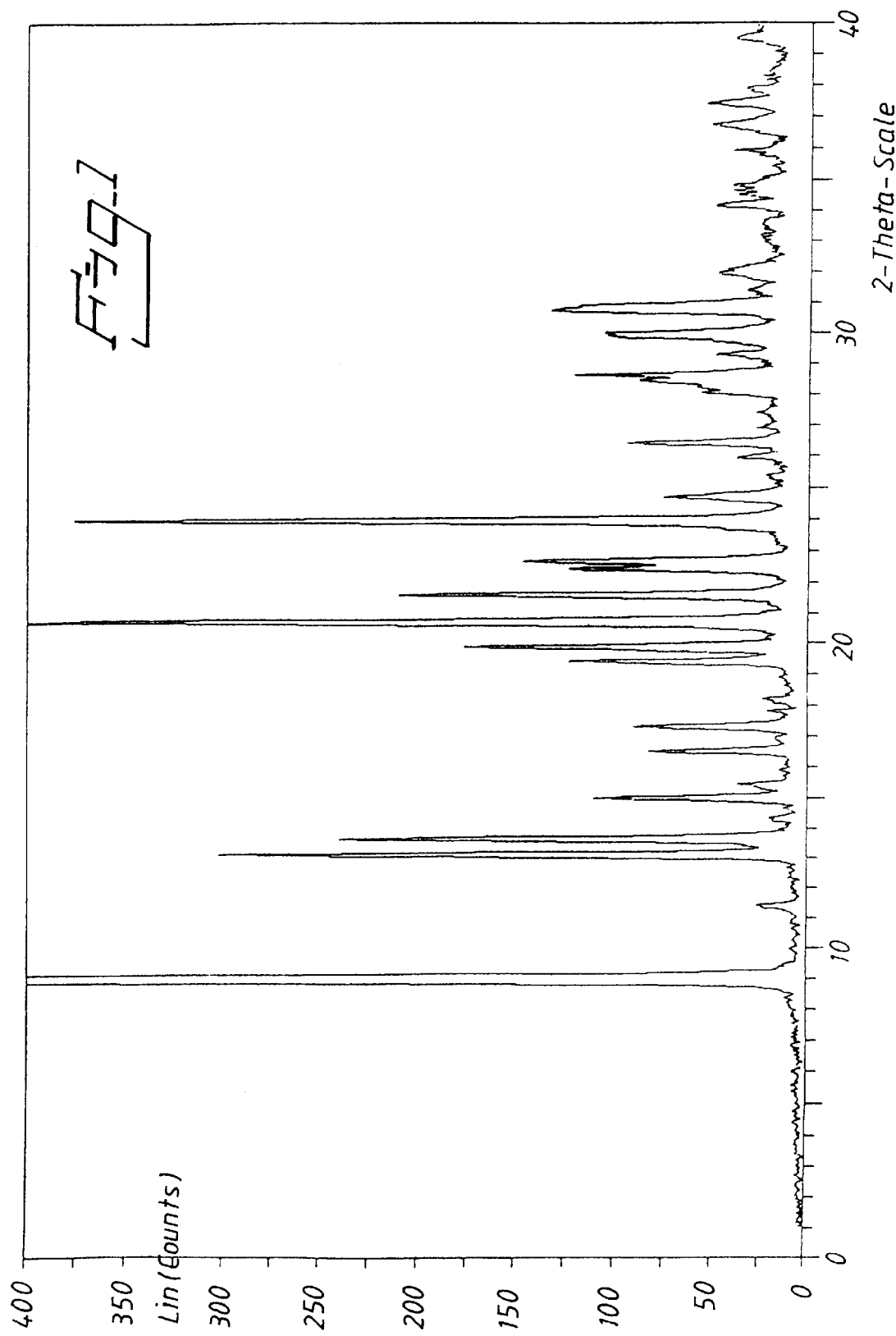

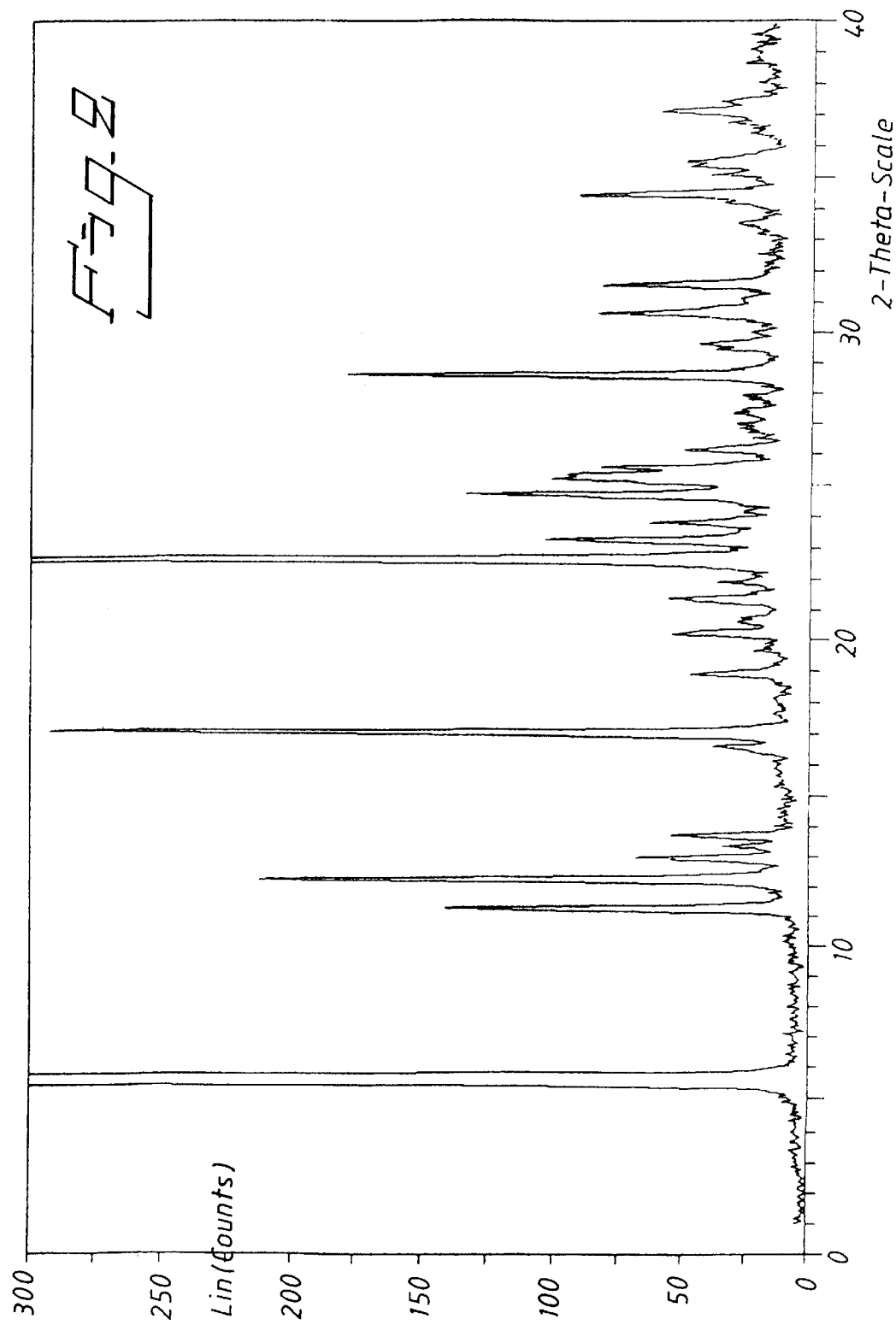

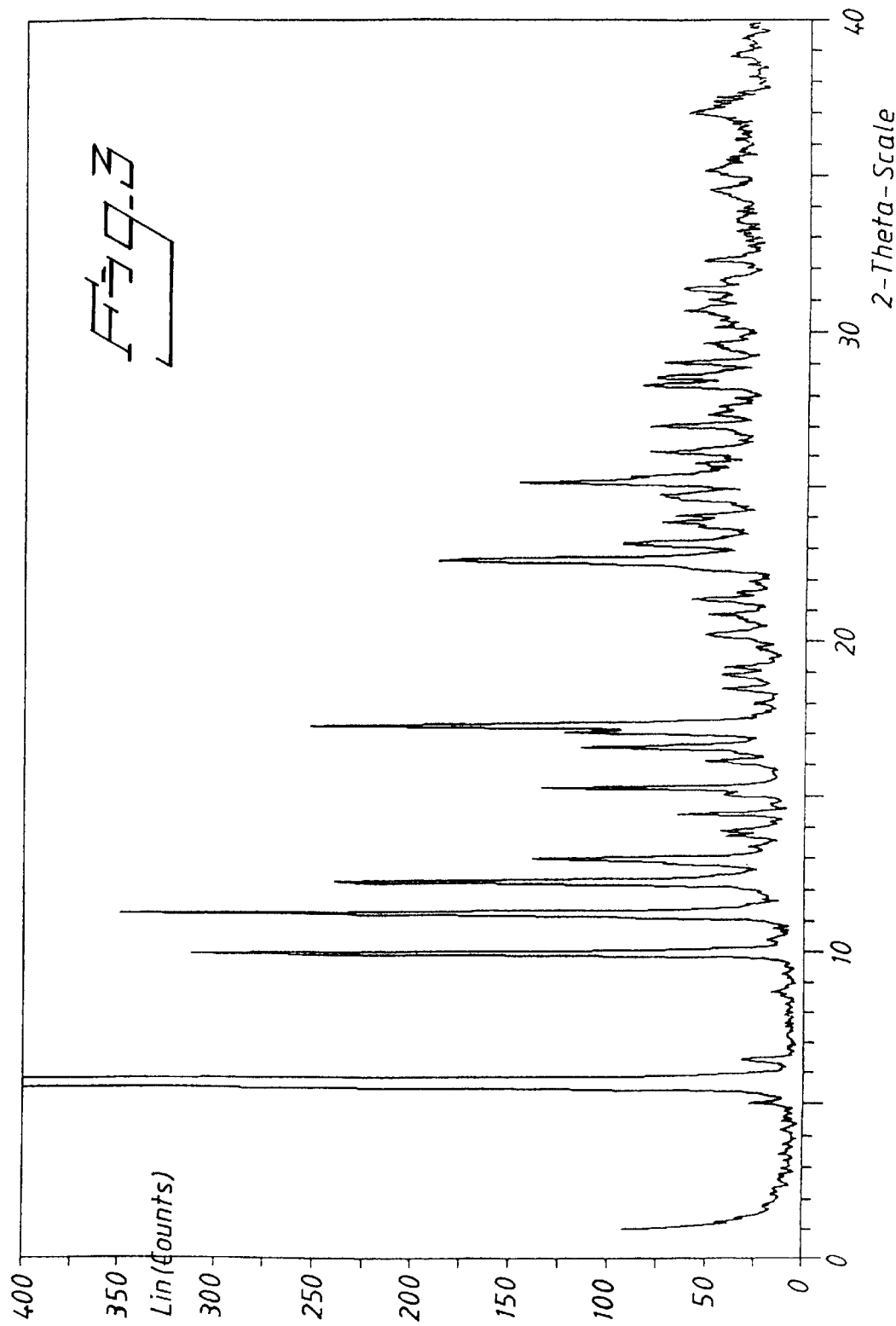

OMEPRAZOLE SODIUM SALT

FIELD OF THE INVENTION

This invention relates to a novel form of 5-methoxy-2-[[(4-methoxy-3,5-dimethyl-2-pyridinyl)methyl]sulfinyl]-1H-benzimidazole, known under the generic name omeprazole. More specifically, it relates to a novel form of the sodium salt of omeprazole, namely a well-defined omeprazole sodium monohydrate salt, hereinafter referred to as omeprazole sodium form B, and its use in the treatment of gastrointestinal disorders, pharmaceutical compositions containing it and preparation thereof.

BACKGROUND OF THE INVENTION AND PRIOR ART

The compound 5-methoxy-2-[[(4-methoxy-3,5-dimethyl-2-pyridinyl)methyl]sulfinyl]-1H-benzimidazole having the generic name omeprazole, as well as therapeutically acceptable salts thereof, are described in EP 5129. The specific alkaline salts of omeprazole, such as the sodium salt, are disclosed in EP 124 495. The omeprazole sodium salt produced according to examples 1 and 2 of EP 124 495 is a mixture of crystal forms and amorphous material. One of the crystal forms present in this mixture, hereinafter referred to as omeprazole sodium form A, is a hydrate with one to two water molecules, of which one water molecule is strongly bound in the crystal structure while the other is easily removed by drying. The resulting dried substance containing one strongly bound water molecule is very hygroscopic and absorbs water rapidly under normal conditions.

Omeprazole is a proton pump inhibitor, i.e. effective in inhibiting gastric acid secretion, and is useful as an antiulcer agent In a more general sense, omeprazole may be used for treatment of gastric-acid related diseases in mammals and especially in man.

BRIEF DESCRIPTION OF THE DRAWINGS

FIG. 1 is an X-ray powder diffractogram of omeprazole sodium form B.

FIG. 2 is an X-ray powder diffractogram of omeprazole sodium form A.

FIG. 3 is an X-ray powder diffractogram of omeprazole sodium prepared according to prior art.

DESCRIPTION OF THE INVENTION

It has surprisingly been found that the sodium salt of omeprazole exists in a number of different crystal forms. It is an object of the present invention to provide a well-defined, thermodynamically stable at ambient temperature, and industrially useful form of omeprazole sodium, namely omeprazole sodium form B. Another object of the present invention is to provide a process for the preparation of omeprazole sodium form B, substantially free from other forms of the sodium salt of omeprazole. X-ray powder diffraction (XRPD) is used as a method of differentiating omeprazole sodium form B from other forms of the sodium salt of omeprazole.

It has been found that the sodium salt of omeprazole may crystallize in at least two different crystal forms, of which omeprazole sodium form B is one. One other form is omeprazole sodium form A with one to two moles of water. Omeprazole sodium form A is one of the crystal forms present in the mixture of crystal forms and amorphous material obtained in example 1 and example 2 in EP 124 495. However, there is no omeprazole sodium form B present in the mixture of forms obtained when preparing omeprazole sodium salt as described in either example 1 or example 2 in EP 124 495.

Omeprazole sodium form B is a crystalline form exhibiting advantageous properties, such as being well-defined, stable, and being a true monohydrate crystal form. Omeprazole sodium form B is thermodynamically more stable than omeprazole sodium form A. Omeprazole sodium form B is essentially non-hygroscopic and can therefore in industrial processes, such as pharmaceutical manufacturing processes, be charged in a fixed amount in contrast to omeprazole sodium form A which must be charged in amounts calculated from a recent assay of omeprazole or indirectly from a recent assay of its water content. Other advantages include easier preparation and higher reproducibility between batches. This is especially important in production scale and leads to a higher production capacity.

Omeprazole sodium form A, which is thermodynamically unstable, can under certain storing conditions be completely or partly converted to omeprazole sodium form B. Omeprazole sodium form B is thereby characterized in being thermodynamically more stable than omeprazole sodium form A and any other form of omeprazole sodium prepared according to prior art. Omeprazole sodium form B is further characterized as being essentially non-hygroscopic.

With the expression "any other form" is meant anhydrates, hydrates, solvates and amorphous materials, including polymorphs disclosed in the prior art. Examples of any other forms of sodium salts of omeprazole includes, but are not limited to, anhydrates, monohydrates, dihydrates, sesquihydrates, trihydrates, alcoholates and polymorphs or amorphous forms thereof.

Omeprazole sodium form B is characterized by the positions and intensities of the peaks in the X-ray powder diffractogram, as well as by the unit cell parameters which have been calculated from the peak positions. The corresponding data for omeprazole sodium form A are totally different, whereas form B is easily distinguishable from form A.

Omeprazole sodium form B according to the present invention is characterized in providing an X-ray powder diffraction pattern exhibiting substantially the following d-values;

| d-value/Å | relative intensity | d-value/Å | relative intensity |
|---|---|---|---|
| 9.8 | vs | 3.37 | w |
| 7.8 | vw | 3.25 | vw |
| 6.7 | s | 3.17 | vw |
| 6.5 | s | 3.14 | w |
| 6.2 | vw | 3.12 | m |
| 5.9 | m | 3.05 | w |
| 5.8 | vw | 2.99 | w |
| 5.4 | w | 2.98 | m |
| 5.1 | w | 2.91 | m |
| 4.6 | m | 2.89 | m |
| 4.5 | m | 2.79 | vw |
| 4.3 | s | 2.62 | vw |
| 4.1 | m | 2.59 | vw |
| 3.96 | m | 2.50 | vw |
| 3.92 | m | 2.45 | vw |
| 3.71 | s | 2.40 | vw |
| 3.60 | w | 2.37 | vw |
| 3.43 | vw | 2.28 | vw |

Omeprazole sodium form B according to the present invention is characterized by having a monoclinic unit cell with parameters $a=15.09\text{Å}$, $b=12.83\text{Å}$, $c=9.82\text{Å}$, $\beta=94.4°$.

According to the invention there is further provided a process for the preparation of omeprazole sodium form B as well as a process for the preparation of omeprazole sodium form A.

Omeprazole sodium form B can also be characterized by FT-IR.

Omeprazole sodium form B is prepared by treating omeprazole with an aqueous base, $Na^+B^-$, wherein Na denotes sodium and B denotes hydroxide or alkoxide, in an appropriate solvent, such as isopropanol optionally containing some water, at ambient temperature. Once the mixing has taken place the total mixture may be agitated, for example stirred, for a further period of time, e.g. about 0–2 hours, at ambient temperature. The crude mixture may optionally be filtered at this stage. Seeds of omeprazole sodium form B may be added to the crystallization solution in order to induce the crystallization. The slurry is thereafter further agitated for a time period of about 10–24 h to ensure as complete crystallization as possible. It is also possible to cool the mixture in order to complete the crystallization and thereby improving the yield The omeprazole sodium form B is thereafter separated, for example by filtration or centrifugation, followed by washing with an appropriate solvent, preferably the same solvent as used above, and thereafter dried to constant weight.

Omeprazole sodium form B may also be prepared by recrystallizing the sodium salt of omeprazole of any form, or mixtures thereof, in an appropriate solvent such as ethanol or isopropanol, optionally containing some water.

The omeprazole sodium form B obtained according to the present invention is substantially free from other forms of sodium salts of omeprazole, such as omeprazole sodium form A.

The compound of the invention, i.e. omeprazole sodium form B, prepared according to the present invention is analyzed, characterized and differentiated from omeprazole sodium form A by X-ray powder diffraction, a technique which is known per se. Another suitable technique to analyze, characterize and differentiate omeprazole sodium form B from omeprazole sodium form A is by conventional FT-IR.

The amount of water in omeprazole sodium form B and omeprazole sodium form A is determined by thermogravimetric analysis, a technique which is known per se. The water content can also be determined by Karl Fischer.

Omeprazole sodium form B is effective as a gastric acid secretion inhibitor, and is useful as an antiulcer agent. In a more general sense, it can be used for treatment of gastric-acid related conditions in mammals and especially in man, including e.g. reflux esophagitis, gastritis, duodenitis, gastric ulcer and duodenal ulcer. Furthermore, it may be used for treatment of other gastrointestinal disorders where gastric acid inhibitory effect is desirable e.g. in patients on NSAID therapy, in patients with Non Ulcer Dyspepsia, in patients with symptomatic gastro-esophageal reflux disease, and in patients with gastrinomas. The compound of the invention may also be used in patients in intensive care situations, in patients with acute upper gastrointestinal bleeding, pre- and postoperatively to prevent aspiration of gastric acid and to treat stress ulceration. Further, the compound of the invention may be useful in the treatment of psoriasis as well as in the treatment of Helicobacter infections and diseases related to these. The compound of the invention may also be used for treatment of inflammatory conditions in mammals, including man.

Any suitable route of administration may be employed for providing the patient with an effective dosage of omeprazole sodium form B according to the invention. For example, peroral or parenteral formulations and the like may be employed. Dosage forms include capsules, tablets, dispersions, solutions, suspensions and the like. Omeprazole sodium form B is, because of it being highly soluble in water, especially suitable for parenteral formulations, such as for intravenous administration.

According to the invention there is further provided a pharmaceutical composition comprising omeprazole sodium form B, as active ingredient, in association with a pharmaceutically acceptable carrier, diluent or excipient and optionally other therapeutic ingredients. Compositions comprising other therapeutic ingredients are especially of interest in the treatment of Helicobacter infections. The invention also provides the use of omeprazole sodium form B in the manufacture of a medicament for use in the treatment of a gastric-acid related condition and a method of treating a gastric-acid related condition which method comprises administering to a subject suffering from said condition a therapeutically effective amount of omeprazole sodium form B.

The compositions of the invention include compositions suitable for peroral or parenteral administration. The compositions may be conveniently presented in unit dosage forms, and prepared by any methods known in the art of pharmacy.

Combination therapies comprising omeprazole sodium form B and other active ingredients in separate dosage forms may also be used. Examples of such active ingredients include anti-bacterial compounds, non-steroidal anti-inflammatory agents, antacid agents, alginates and prokinetic agents.

In the practice of the invention, the most suitable route of administration as well as the magnitude of a therapeutic dose of omeprazole sodium form B in any given case will depend on the nature and severity of the disease to be treated. The dose, and dose frequency, may also vary according to the age, body weight, and response of the individual patient. Special requirements may be needed for patients having Zollinger-Ellison syndrome, such as a need for higher doses than the average patient. Children and patients with liver diseases as well as patients under long term treatment will generally benefit from doses that are somewhat lower than the average. Thus, in some conditions it may be necessary to use doses outside the ranges stated below. Such higher and lower doses are within the scope of the present invention.

In general, a suitable dose range for parental administration is from 10 mg to 300 mg, and preferably from 20 mg to 80 mg.

A suitable oral dosage form may cover a dose range from 5 mg to 300 mg total daily dose, administered in one single dose or equally divided doses. A preferred dosage range is from 10 mg to 80 mg.

The compound of the invention may be combined as the active component in intimate admixture with a pharmaceutical carrier according to conventional techniques, such as the oral formulations described in WO 96/01623 and EP 247 983, the disclosures of which are hereby incorporated as a whole by reference.

The examples which follow will further illustrate the preparation of the compound of the invention, i.e. omeprazole sodium form B, but are not intended to limit the scope of the invention as defined hereinabove or as claimed below.

EXAMPLES

Example 1

Preparation of omeprazole sodium form B from omeprazole 120 gram of omeprazole, 480 ml of isopropanol and 13.2 gram of NaOH(s) dissolved in 26.7 gram of water, was added to a 3-necked glass vessel. The slurry was stirred for an additional 40 minutes at ambient room temperature. The obtained solution was filtered through a clarifying filter and the filter was washed with 20 ml of isopropanol. The isopropanol wash was combined with the previous isopropanol solution containing the product. The solution was seeded with 6 gram of omeprazole sodium form B in 25 ml of isopropanol. The slurry was stirred for an additional 25 hours and the product was filtered and dried at 40° C.

Yield 84.5%.

Example 2

Preparation of omeprazole sodium form B from omeprazole sodium form A 30 gram of omeprazole sodium form A, prepared according to example 3 below, and 25 ml of ethanol was added to a 3-necked glass vessel. The slurry was seeded with omeprazole sodium form B and then stirred for an additional 24 hours at room temperature. The product was then filtered and dried at 50° C.

Yield: 80%

Example 3

Preparation of omeprazole sodium form A from omeprazole 14.8 kg sodium hydroxide was dissolved in 42 l water in a separate vessel.

120 kg omeprazole was added to 927 l isopropanol in a 4000 l glass lined reactor. The aqueous sodium hydroxide was charged to the slurry. Omeprazole was dissolved and the clear solution was filtered in a closed pressure filter to a 1200 l glass lined reactor. The solution was heated and 228 l methanol was charged at 50° C. to initiate the crystallization. The batch was seeded with a slurry of 1.2 kg omeprazole sodium methanol wet in isopropanol. The solution was cooled from 51° C. to −8° C. The formed slurry was kept at −8 to −9° C. for 4 hours with moderate stirring. Centrifuged substance was flushed with a cool mixture of isopropanol and methanol, 76 l and 20 l respectively, and then dried in a rotary dryer at approximately 35 mbar with a jacket temperature of 65° C. Dried substance was de-lumped in a mill.

Yield: 126.0 kg omeprazole sodium methanol wet.

A sample of the omeprazole sodium methanol wet (32.3 kg) was charged into a rotary dryer. An equilibration process with steam in order to remove methanol was performed at 39–87 mbar and with a jacket temperature of 50° C. The equilibration process took 3 days. Equilibrated substance was de-lumped in a mill.

Yield: 25.7 kg

Example 4

Characterization of omeprazole sodium form B and omeprazole sodium form A using X-ray powder diffraction (XRPD)

X-ray powder diffraction analysis was performed according to standard methods which can be found in e.g. Bunn, C. W. (1948), Chemical Crystallography, Clarendon Press, London; or Klug, H. P. & Alexander, L. E. (1974), X-Ray Diffraction Procedures, John Wiley and Sons, New York. The unit cell parameters for form A and B have been calculated from the X-ray powder diffractograms using the program "TREOR" by Werner, P.-E., Eriksson,L. And Westdahl, M., J. Appl. Crystallogr. 18 (1985) 367–370. The fact that the positions of all peaks in the diffractograms for form A and form B may be calculated using the respective unit cell parameters, proves that the unit cells are correct and that the diffractograms are indicative of the pure forms. The diffractogram of omeprazole sodium form B, prepared according to Example 1 in the present application, is shown in FIG. 1 and the diffractogram of omeprazole sodium form A, prepared according to Example 3, is shown in FIG. 2.

The peaks, identified with d-values calculated from the Bragg formula and intensities, have been extracted from the diffractograms for form A, form B and from the diffractogram obtained from material produced according to prior art, and are given in Table 1. In this table the unit cell parameters for forms A and B are also given. The relative intensities are less reliable and instead of numerical values the following definitions are used;

| % Relative Intensity | Definition |
| --- | --- |
| 25–100 | vs (very strong) |
| 10–25 | s (strong) |
| 3–10 | m (medium) |
| 1–3 | w (weak) |
| <1 | vw (very weak) |

Some additional very weak peaks found in the diffractograms have been omitted from table 1.

Reference Example A

Preparation of omeprazole sodium according to prior art in accordance with the method described in Example 2 in EP 124 495

Omeprazole (1300 g; 3.77 mol) was added under vigorous mechanical stirring to a mixture of tetrahydrofurane (13 L) and 50% aqueous NaOH (296 g, 3.7 mol) and stirring was continued for 45 min. Trichloroethylene (5.7 L) was added and stirring was continued over night at room temperature. The mixture was cooled to +5° C. and then stirred for 3 h. The precipitate was filtered off and the filter cake was washed with trichloroethylene (5 L) and dried under reduced pressure at 50° C. giving omeprazole sodium salt (1314 g, 95%), m.p. 208–210 ° C.

The product was analyzed using X-ray powder diffraction and gave the diffractogram depicted in FIG. 3 and given above in Table 1. Some additional very weak peaks found in the diffractograms have been omitted from Table 1.

TABLE 1

X-ray powder diffraction data for omeprazole sodium form A, form B and according to prior art. Only peaks below 2θ = 40° have been included. All peaks noted for form A and form B can be indexed with the unit cells given below.

Unit cell form A:
a = 15.757 (3) Å
b = 8.126 (1) Å
c = 15.671 (6) Å
β = 94.21 (2)°

Unit cell form B:
a = 15.086 (6) Å
b = 12.835 (4) Å
c = 9.815 (3) Å
β = 94.41 (3)°

| Omeprazole sodium form A | | Omeprazole sodium form B | | Omeprazole sodium according to prior art | |
| --- | --- | --- | --- | --- | --- |
| d-value/Å | Relative intensity | d-value/Å | relative intensity | d-value/Å | Relative intensity |
| | | | | 17.8 | vw |
| 15.6 | vs | 9.8 | vs | 15.5 | vs |
| | | | | 13.9 | vw |
| | | | | 10.2 | vw |
| | | | | 8.9 | m |
| 7.9 | m | 7.8 | vw | 8.0 | m |
| 7.2 | m | 6.7 | s | 7.2 | m |
| | | | | 6.9 | w |
| 6.8 | w | 6.5 | s | 6.8 | w |
| 6.6 | vw | 6.2 | vw | | |
| 6.5 | w | 5.90 | m | 6.5 | vw |
| | | | | 6.4 | vw |
| | | | | 6.2 | vw |
| | | | | 5.91 | vw |
| | | | | 5.83 | w |
| | | | | 5.52 | vw |
| 5.35 | vw | 5.76 | vw | 5.37 | w |
| 5.20 | s | 5.36 | w | 5.21 | w |
| | | | | 5.15 | m |
| | | | | 4.81 | vw |

TABLE 1-continued

X-ray powder diffraction data for omeprazole sodium form A, form B and according to prior art. Only peaks below 2θ = 40° have been included. All peaks noted for form A and form B can be indexed with the unit cells given below.

Unit cell form A:
a = 15.757 (3) Å
b = 8.126 (1) Å
c = 15.671 (6) Å
β = 94.21 (2)°

Unit cell form B:
a = 15.086 (6) Å
b = 12.835 (4) Å
c = 9.815 (3) Å
β = 94.41 (3)°

| Omeprazole sodium form A | | Omeprazole sodium form B | | Omeprazole sodium according to prior art | |
|---|---|---|---|---|---|
| d-value/Å | Relative intensity | d-value/Å | relative intensity | d-value/Å | Relative intensity |
| 4.70 | vw | 5.12 | w | 4.70 | vw |
|  |  |  |  | 4.63 | vw |
| 4.40 | vw | 4.57 | m | 4.40 | vw |
| 4.29 | vw | 4.46 | m |  |  |
|  |  |  |  | 4.27 | vw |
| 4.17 | vw | 4.29 | s | 4.17 | vw |
| 3.935 | s | 4.11 | m | 3.938 | w |
|  |  |  |  | 3.846 | vw |
| 3.831 | w | 3.963 | m |  |  |
| 3.744 | w | 3.920 | m | 3.748 | vw |
|  |  |  |  | 3.711 | vw |
| 3.611 | w | 3.713 | s | 3.610 | vw |
| 3.543 | w | 3.601 | w | 3.545 | w |
| 3.522 | w | 3.431 | vw | 3.519 | vw |
| 3.488 | w | 3.375 | w |  |  |
|  |  |  |  | 3.464 | vw |
| 3.411 | vw | 3.254 | vw | 3.410 | vw |
|  |  |  |  | 3.304 | vw |
|  |  |  |  | 3.256 | vw |
|  |  |  |  | 3.151 | vw |
| 3.125 | m | 3.173 | vw | 3.125 | vw |
|  |  |  |  | 3.079 | vw |
| 3.021 | vw | 3.137 | w | 3.026 | vw |
| 2.919 | w | 3.119 | m | 2.911 | vw |
|  |  |  |  | 2.854 | vw |
| 2.833 | w | 3.050 | w |  |  |
|  |  |  |  | 2.775 | vw |
| 2.676 | vw | 2.993 | w |  |  |
| 2.626 | vw | 2.980 | m |  |  |
| 2.606 | vw | 2.906 | m | 2.601 | vw |
|  |  |  |  | 2.553 | vw |
| 2.534 | vw | 2.892 | m |  |  |
| 2.425 | vw | 2.793 | vw | 2.430 | vw |
|  |  | 2.624 | vw |  |  |
|  |  | 2.589 | vw |  |  |
|  |  | 2.499 | vw |  |  |
|  |  | 2.447 | vw |  |  |
|  |  | 2.402 | vw |  |  |
|  |  | 2.372 | vw |  |  |
|  |  | 2.283 | vw |  |  |

What is claimed is:

1. Omeprazole sodium form B having an X-ray powder diffraction pattern exhibiting substantially the following d-values and intensities:

| d-value/Å | relative intensity |
|---|---|
| 9.8 | vs |
| 7.8 | vw |
| 6.7 | s |
| 6.5 | s |
| 6.2 | vw |
| 5.9 | m |
| 5.8 | vw |
| 5.4 | w |
| 5.1 | w |
| 4.6 | m |
| 4.5 | m |
| 4.3 | s |
| 4.1 | m |
| 3.96 | m |
| 3.92 | m |
| 3.71 | s |
| 3.60 | w |
| 3.43 | vw |
| 3.37 | w |
| 3.25 | vw |
| 3.17 | vw |
| 3.14 | w |
| 3.12 | m |
| 3.05 | w |
| 2.99 | w |
| 2.98 | m |
| 2.91 | m |
| 2.89 | m |
| 2.79 | vw |
| 2.62 | vw |
| 2.59 | vw |
| 2.50 | vw |
| 2.45 | vw |
| 2.40 | vw |
| 2.37 | vw |
| 2.28 | vw. |

2. The compound according to claim 1, wherein omeprazole sodium form B is defined by a monoclinic unit cell with parameters $$a=15.09(4) \text{ Å}, b=12.83\text{Å}, c=9.82\text{Å}, \beta=94.4°.$$

3. A process for the preparation of omeprazole sodium form B according to claim 1 comprising the steps:

a) adding an aqueous $Na^+B^-$base to omeprazole in a solvent mixture comprising an alcohol and water, b) allowing the solution to crystallize, and c) isolating the omeprazole sodium form B thus obtained.

4. A process according to claim 3 wherein the alcohol is isopropanol.

5. A process for the preparation of omeprazole sodium form B according to claim 1 comprising the steps:

a) dissolving omeprazole sodium of any form, or a mixture thereof, in a solvent mixture comprising alcohol and water, b) allowing the solution to crystallize, and c) isolating the omeprazole sodium form B thus obtained.

6. A pharmaceutical formulation comprising omeprazole sodium form B according to claim 1 in admixture with a pharmaceutically acceptable excipient.

7. A pharmaceutical formulation suitable for intravenous administration comprising omeprazole sodium form B according to claim 1 in admixture with a pharmaceutically acceptable excipient.

8. A method of treatment of gastrointestinal disorders which comprises administration of a therapeutically effective amount of omeprazole sodium form B according to claim 1 to a patient suffering from gastrointestinal disorders.

9. The process according to claim 3 or 5, wherein omeprazole sodium form B is used to induce crystallization.

* * * * *